(12) United States Patent
Taniike et al.

(10) Patent No.: US 7,741,125 B2
(45) Date of Patent: Jun. 22, 2010

(54) BIOSENSOR, BIOSENSOR MEASURING APPARATUS AND MEASUREMENT METHOD

(75) Inventors: Yuko Taniike, Osaka (JP); Mariko Miyashita, Hyogo (JP); Toshihiko Yoshioka, Kanagawa (JP)

(73) Assignee: Panasonic Corporation, Osaka (JP)

(*) Notice: Subject to any disclaimer, the term of this patent is extended or adjusted under 35 U.S.C. 154(b) by 1267 days.

(21) Appl. No.: 10/550,150

(22) PCT Filed: Feb. 2, 2005

(86) PCT No.: PCT/JP2005/001482

§ 371 (c)(1),
(2), (4) Date: Sep. 21, 2005

(87) PCT Pub. No.: WO2005/075979

PCT Pub. Date: Aug. 18, 2005

(65) Prior Publication Data

US 2006/0188395 A1    Aug. 24, 2006

(30) Foreign Application Priority Data

Feb. 4, 2004    (JP) .................... 2004-028618

(51) Int. Cl.
    *G01N 33/18* (2006.01)
(52) U.S. Cl. .................. 436/169; 422/58; 422/61; 422/68.1
(58) Field of Classification Search ............. 422/58, 422/61, 68.1; 436/169
See application file for complete search history.

(56) References Cited

U.S. PATENT DOCUMENTS

| 5,266,179 A | 11/1993 | Nankai et al. |
| 5,843,691 A * | 12/1998 | Douglas et al. ............... 435/14 |
| 2008/0118399 A1 * | 5/2008 | Fleming ................... 422/68.1 |

FOREIGN PATENT DOCUMENTS

| EP | 1 146 332 A1 | 10/2001 |
| JP | 58-199020 | 11/1983 |
| JP | 1-153941 | 6/1989 |
| JP | 03-202764 | 9/1991 |
| JP | 05-005736 | 1/1993 |
| JP | 2002-014072 | 1/2002 |
| JP | 2002-340886 | 11/2002 |
| JP | 2002-355297 | 12/2002 |
| JP | 2003-302314 | 10/2003 |

* cited by examiner

*Primary Examiner*—Lyle A Alexander
(74) *Attorney, Agent, or Firm*—McDermott Will & Emery LLP

(57) ABSTRACT

A biosensor and a biosensor measuring apparatus whose performance can be easily determined by an ordinary user are provided. A biosensor 100 includes a substrate 1 having a quality deciding section 13 and a sample receiving section 15 provided on the substrate 1 to which a sample is supplied. The quality deciding section 13 includes a moisture absorbing material changed in color through absorption of moisture. The sample receiving section 15 has a reagent section 7 including an enzyme reacted with a test substance as a substrate. The quality deciding section 13 includes a recess 17 formed in the substrate 1, the moisture absorbing material 16 disposed in the recess 17 and a film 18 with no air permeability substantially covering the opening of the recess 17 and closely adhered to the moisture absorbing material 16. Cobalt salt is used as the moisture absorbing material 16.

10 Claims, 9 Drawing Sheets

FIG. 2
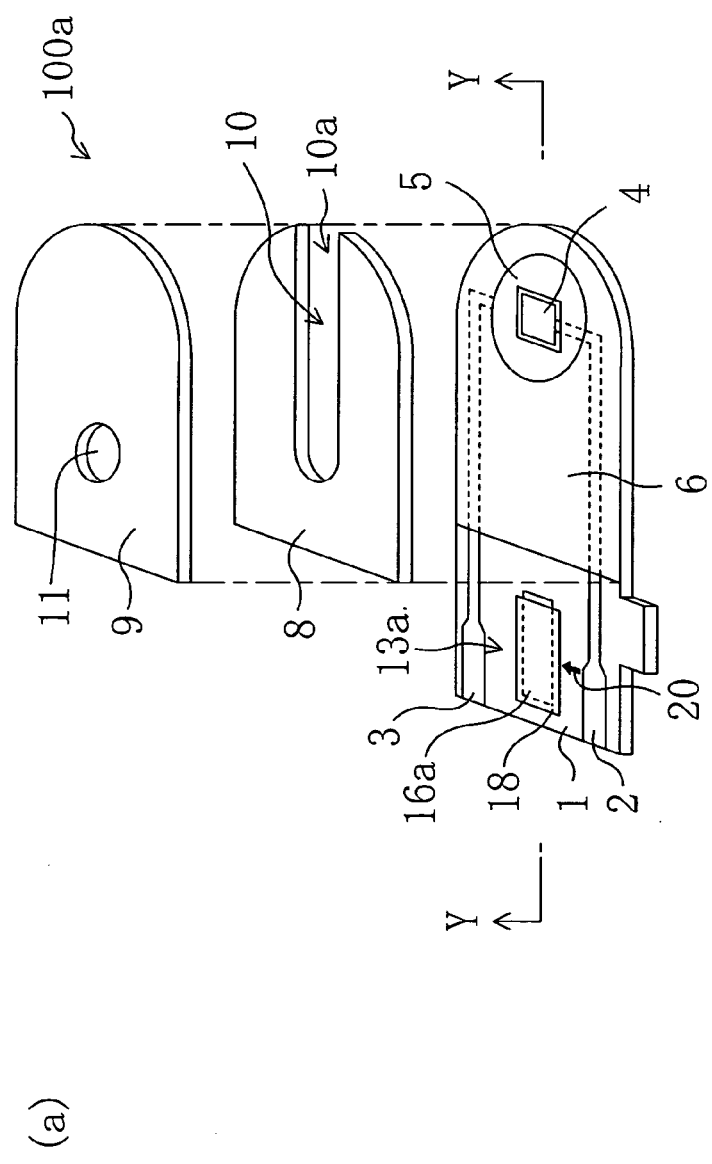
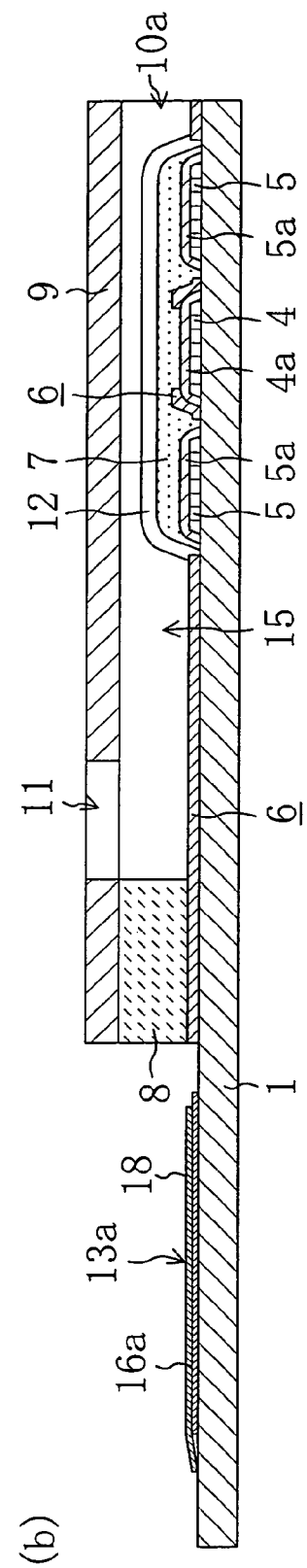

FIG. 3
(a) 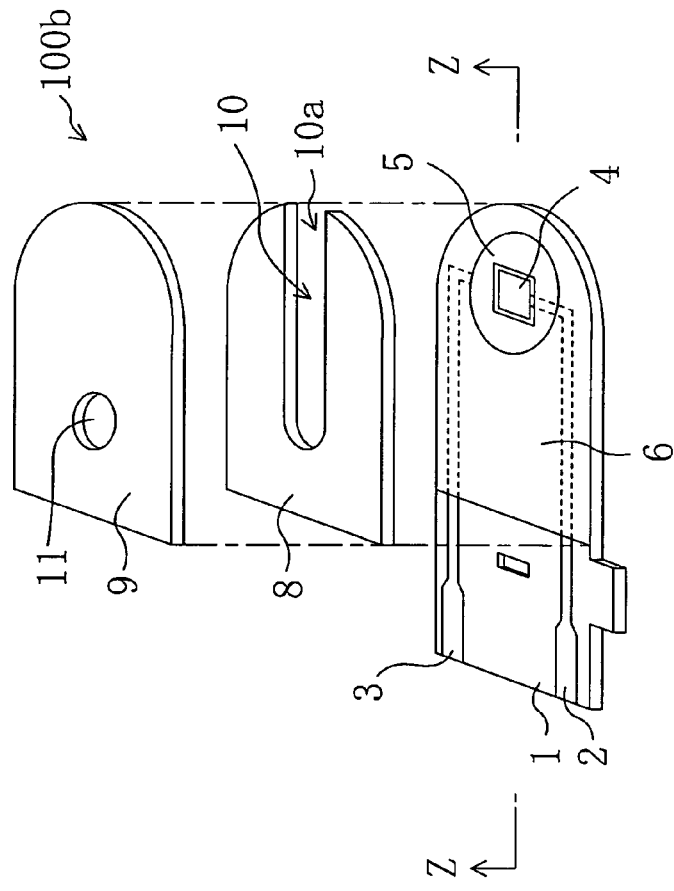
(b) 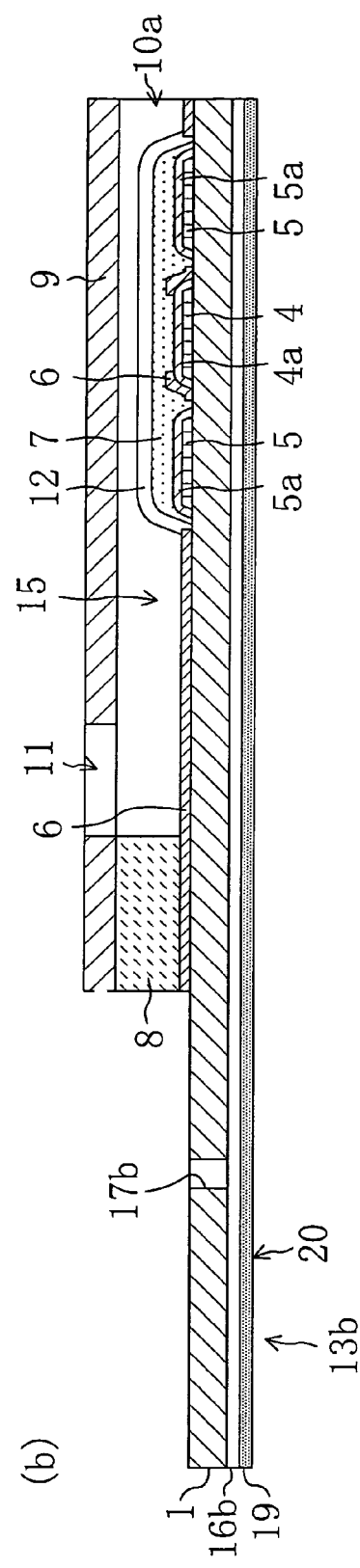

FIG. 4
(a) 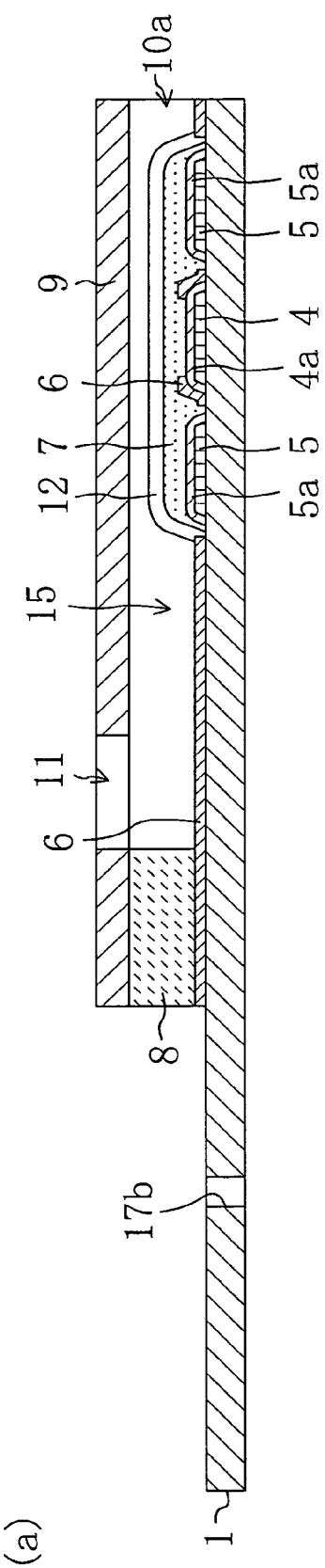
(b) 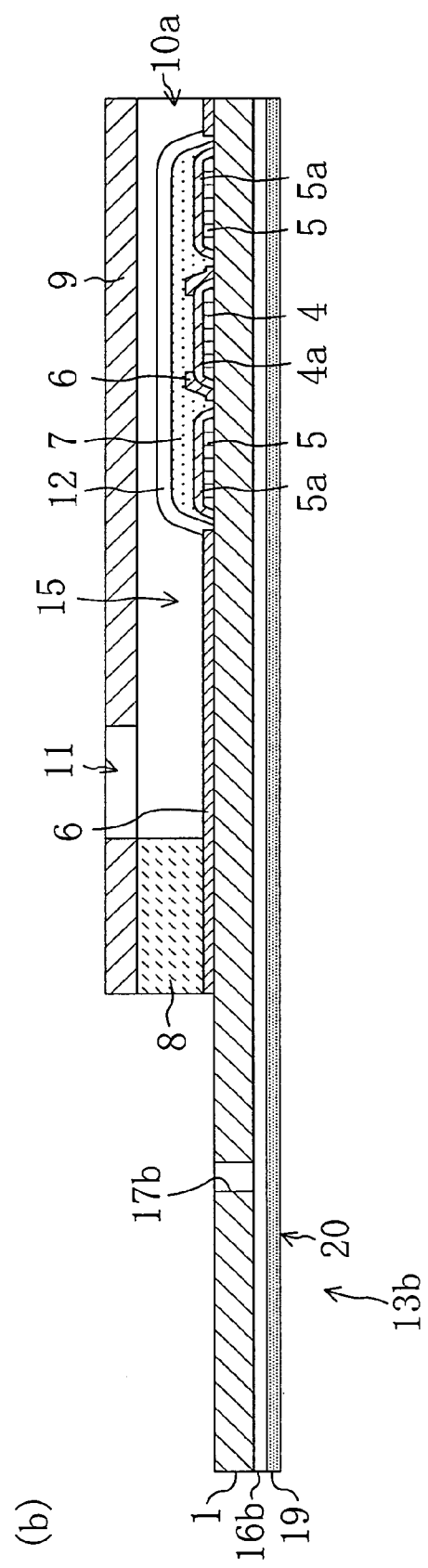

FIG. 6
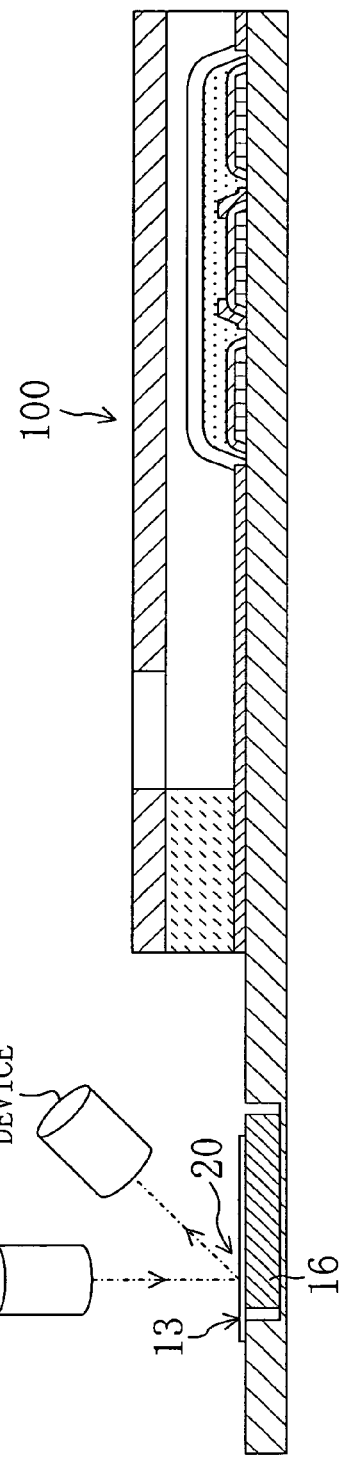
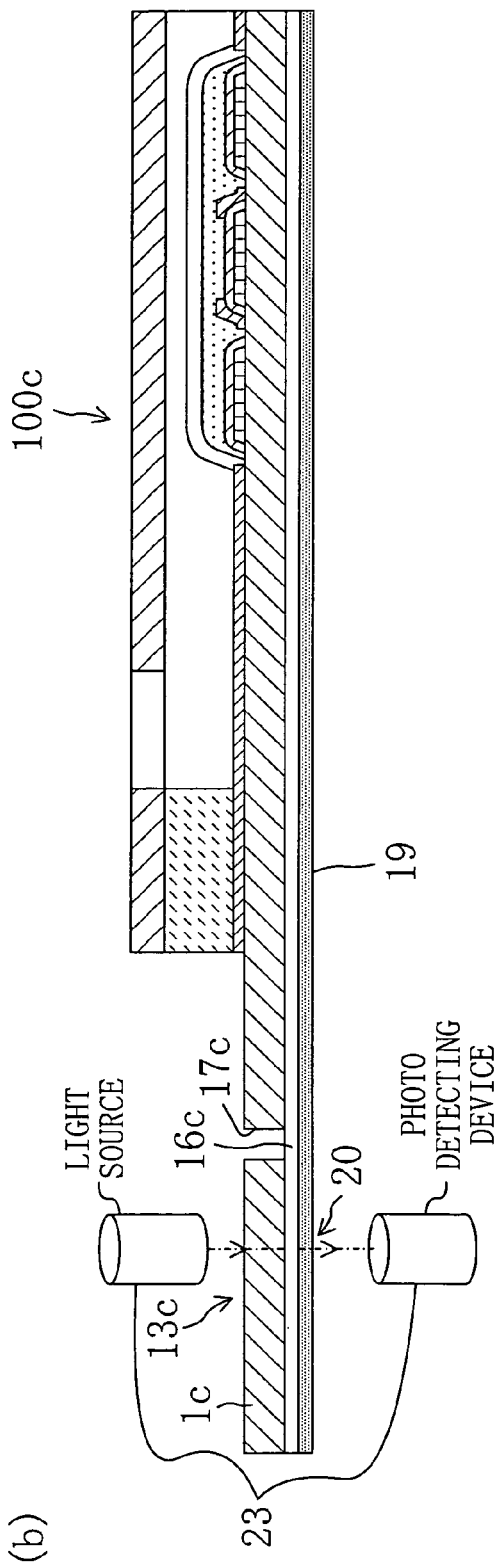

FIG. 8
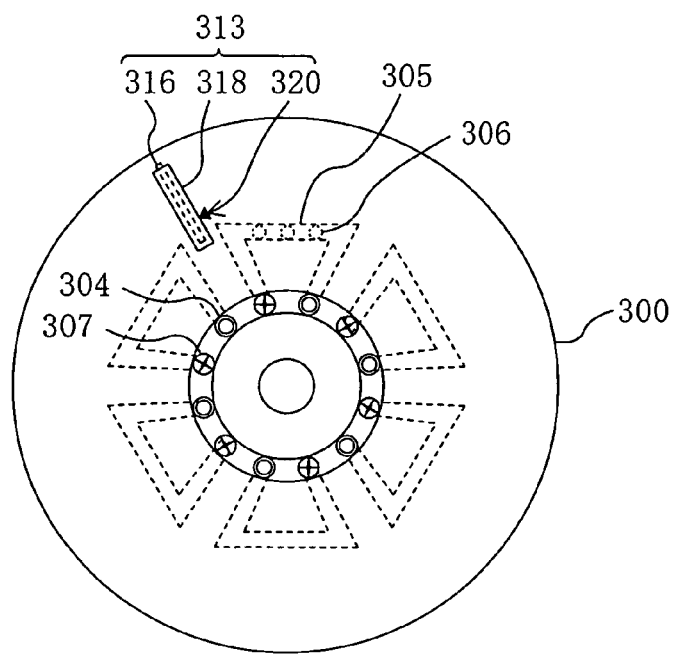
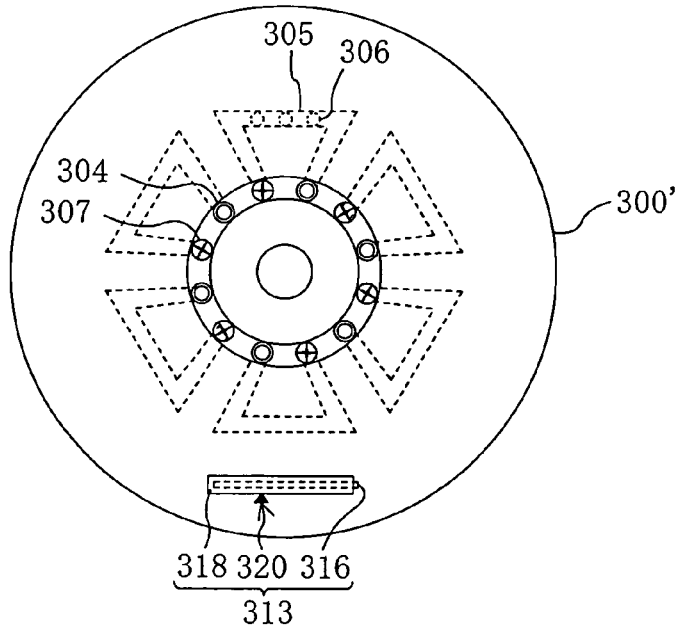
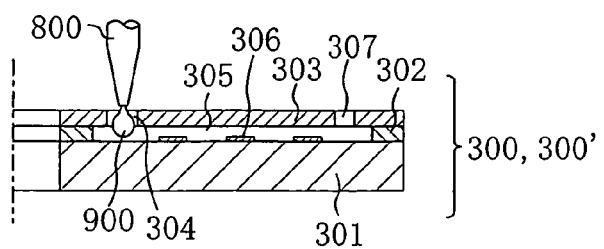

US 7,741,125 B2

BIOSENSOR, BIOSENSOR MEASURING APPARATUS AND MEASUREMENT METHOD

RELATED APPLICATION

This application is the U.S. National Phase under 35 U.S.C. §371 of International Application No. PCT/JP2005/001482, filed Feb. 2, 2005, which in turn claims the benefit of Japanese Application No. 2004-028618, filed Feb. 4, 2004, the disclosures of which Applications are incorporated by reference herein in their entirety.

TECHNICAL FIELD

The present invention relates to a biosensor for more accurately measuring a test substance included in a sample.

BACKGROUND ART

Recently, various types of biosensors using a specific catalysis function of an enzyme have been developed as a quantitative analysis method for a saccharide such as sucrose or glucose.

Now, a quantitative analysis method for glucose will be described as an example of the quantitative analysis method for a saccharide included in a sample. As an electrochemical quantitative analysis method for glucose, a method using an enzyme of glucose oxidase (EC1.1.3.4; hereinafter abbreviated as GOD) and an oxygen electrode or a hydrogen peroxide electrode is generally known.

GOD selectively oxidizes a substrate of β-D-glucose into D-glucono-δ-lactone by using oxygen as an electron mediator. In the oxidation reaction caused by GOD in the presence of oxygen, oxygen is reduced to hydrogen peroxide. The amount of thus reduced oxygen is measured with the oxygen electrode or the amount of thus increased hydrogen peroxide is measured with the hydrogen peroxide electrode. The amount of reduced oxygen or the amount of increased hydrogen peroxide is proportional to the content of glucose in a sample, and therefore, the glucose is measured on the basis of the amount of reduced oxygen or the amount of increased hydrogen peroxide.

In the aforementioned method, the glucose included in the sample can be accurately measured by utilizing the specificity of the enzyme reaction. However, as is presumed from the reaction process, this method has a disadvantage that it is largely affected by the concentration of oxygen included in the sample, and when the sample includes no oxygen, the measurement cannot be performed.

Therefore, a glucose measuring biosensor using, as an electron mediator, not oxygen but an organic compound or a metal complex such as potassium ferricyanide, a ferrocene derivative or a xenon derivative has been developed. In this glucose measuring biosensor, a reductant of the electron mediator resulting from an enzyme reaction is oxidized on a working electrode, thereby obtaining the concentration of glucose included in a sample on the basis of an oxidation current flowing in the oxidation. At this point, a reaction in which an oxidant of the electron mediator is reduced so as to generate the reductant of the electron mediator is proceeded on a counter electrode. When an organic compound or a metal complex is thus used as an electron mediator instead of oxygen, a reagent section can be formed by stably and accurately holding a known amount of GOD and the electron mediator on the electrode, and therefore, glucose can be accurately measured without being affected by the concentration of oxygen included in the sample. Also, since the reagent section including the enzyme and the electron mediator can be integrated with an electrode system in an almost dry state in this case, a disposable glucose measuring biosensor based on this technique is recently regarded remarkable. A typical example of such a biosensor is a biosensor described in Patent Document 1, Japanese Laid-Open Patent Publication No. 3-202764. In using a disposable glucose measuring biosensor, the concentration of glucose can be easily measured with a measuring apparatus by simply introducing a sample into the sensor removably connected to the measuring apparatus.

Exemplified measuring procedures for a blood glucose level (that is, a glucose concentration in blood) using the aforementioned disposable glucose measuring biosensor will be described.

First, a measurer takes a glucose measuring biosensor out of a package containing a desiccant and fits it on a measuring apparatus. Thereafter, blood obtained by, for example, tapping a finger tip or the like with a needle is applied on the glucose measuring biosensor, and after a given period of time, the blood glucose level of the measurer is displayed on a displaying section of the measuring apparatus.

Patent Document 1: Japanese Laid-Open Patent Publication No. 3-202764

PROBLEMS TO BE SOLVED BY THE INVENTION

For example, in the aforementioned glucose measuring biosensor, a reagent including an enzyme and an electron mediator is held in the reagent section in a dry state. When the reagent section absorbs the moisture of the air, however, it is apprehended that a part of the enzyme included in the reagent section is inactivated or that an organic compound or a metal complex used as the electron mediator is reformed. Also, the moisture of the air may not only inactivate the enzyme or reform the electron mediator but also affect the reaction of the enzyme or the electron mediator. Therefore, in using the aforementioned glucose measuring biosensor, it is strongly recommended for accurate measurement that the biosensor is taken out of the package immediately before the measurement, but it is given into the hands of a measurer to determine when the biosensor is to be taken out.

In using conventional biosensors including the aforementioned glucose measuring biosensor, however, it is difficult for an ordinary user to determine the performance of a biosensor taken out of its package or the like.

The present invention was devised in consideration of these circumstances, and an object is providing a biosensor and a biosensor measuring apparatus whose performance can be easily determined by an ordinary user.

DISCLOSURE OF THE INVENTION

The biosensor of this invention for measuring a test substance included in a sample includes a substrate; a sample receiving section provided on the substrate to which the sample is supplied; a reagent section provided in the sample receiving section and including a reagent to be reacted with the test substance; and a moisture absorbing material that is changed in color through absorption of moisture, and a degree of degradation of the reagent is shown on the basis of a proportion of a portion of the moisture absorbing material changed in color.

In the case where the biosensor of this invention is packed in, for example, an arbitrary package in the form of distribution, after it is taken out of the package, as it is exposed to the air for a longer time, the moisture absorbing material absorbs moisture of the air, and hence, the moisture absorbing material is changed in color from its portion exposed to the air through a reaction with the absorbed moisture. Accordingly, a user can make the following decision: The measurement is performed before a portion of the moisture absorbing material of the biosensor reaches a given proportion, and if the color changed portion of the moisture absorbing material of the biosensor exceeds the given proportion, it is determined that the reagent section has been degraded, so as not to use the biosensor but exchange it with a new biosensor. Accordingly, an ordinary user can always easily use a biosensor with performance suitable for use without necessity of special knowledge and technique, and hence, accurate measurement can be always performed.

The biosensor may further include a cover for covering the moisture absorbing material, and a part of the moisture absorbing material may be exposed.

The degree of degradation of the reagent may be shown on the basis of a degree of color change of a portion of the moisture absorbing material that is present at a given distance from the exposed part and is covered with the cover.

The reagent may include an enzyme.

The reagent section may further include an electron mediator.

The biosensor may further include a pair of terminals provided on the substrate; and a pair of electrodes provided in the sample receiving section to be spaced from each other and respectively connected to the pair of terminals.

The reagent may include at least one of an antibody and an antigen.

The moisture absorbing material may be in the shape of a sheet.

The biosensor may further include a covering member made of a light blocking material and formed over the substrate for covering the sample receiving section.

The moisture absorbing material in the shape of a sheet may be provided on a face of the substrate opposite to a face thereof on which the sample receiving section is provided, and a sheet for covering the moisture absorbing material may be provided on the moisture absorbing material.

The biosensor measuring apparatus of this invention for measuring a test substance included in a sample by using a biosensor including a substrate; a sample receiving section provided on the substrate and containing a reagent section including a reagent to be reacted with the test substance; and a moisture absorbing material changed in color through absorption of moisture, includes a detecting section including a light source for irradiating the moisture absorbing material with light and a photo detecting device for receiving incident light emitted from the light source through the moisture absorbing material; and a measuring section connected to the detecting section for measuring an optical characteristic of the incident light and for determining a degree of degradation of the reagent included in the reagent section of the biosensor on the basis of the optical characteristic of the incident light.

In using the biosensor measuring apparatus of this invention, the degree of degradation of the reagent is determined by detecting the color change of the moisture absorbing material of the biosensor, and therefore, it can be determined whether or not the biosensor is suitable for use. Accordingly, when the biosensor and the biosensor measuring apparatus are used, a measurer can automatically perform accurate measurement without necessity of special knowledge.

The measurement method of this invention for measuring a test substance included in a sample by using a biosensor including a substrate; a sample receiving section provided on the substrate and containing a reagent section including a reagent to be reacted with the test substance; and a moisture absorbing material changed in color through absorption of moisture, include a step of fitting the biosensor on a biosensor measuring apparatus; a determining step of determining a degree of degradation of the reagent on the basis of a degree of color change of the moisture absorbing material; and a step of measuring the test substance when the degree of degradation of the reagent is determined to be small in the determining step and stopping to measuring the test substance when the degree of degradation of the reagent is determined to be large.

In using the measurement method of this invention, the degree of degradation of the reagent is determined by detecting the color change of the moisture absorbing material of the biosensor, and therefore, after determining whether or not the biosensor is suitable for use by using the biosensor measuring apparatus, the measurement of the test substance can be stopped when the degree of degradation of the reagent is large. Accordingly, when the measurement method of this invention is employed, a measurer can automatically perform accurate measurement without necessity of special knowledge.

EFFECT OF THE INVENTION

The present invention provides a biosensor in which a user can easily determine whether or not its performance is suitable for use, and a biosensor measuring apparatus and a measurement method using the same.

BRIEF DESCRIPTION OF DRAWINGS

FIG. 2A is an exploded perspective view of a biosensor according to Embodiment 2 and FIG. 2B is a cross-sectional view thereof taken on line Y-Y of FIG. 2A.

FIG. 3A is an exploded perspective view of a biosensor according to Embodiment 3 and FIG. 3B is a cross-sectional view thereof taken on line Z-Z of FIG. 3A.

FIGS. 4A and 4B are cross-sectional views for showing procedures in a method for fabricating the biosensor of Embodiment 3.

FIGS. 6A and 6B are schematic cross-sectional views for showing an operation of the biosensor measuring apparatus of Embodiment 4 for measurement with a biosensor.

FIGS. 8A and 8B are plan views of a biosensor according to Embodiment 6 and FIG. 8C is a cross-sectional view of a principal part of FIGS. 8A and 8B.

DESCRIPTION OF NUMERALS

Figure 1:
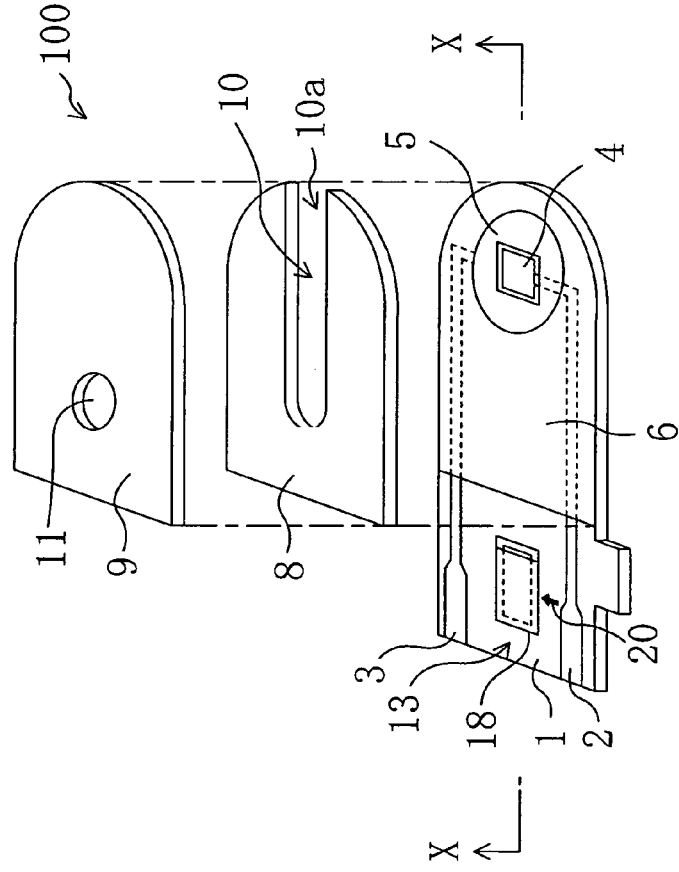
FIG. 1A is an exploded perspective view of a biosensor according to Embodiment 1 and FIG. 1B is a cross-sectional view thereof taken on line X-X of FIG. 1A.

1: substrate
2,3: terminals
4, 5: electrodes 4a, 5a: conductive carbon pastes
6: insulating film
7: reagent section
8: spacer member
9: protecting plate
10: slit
10a: sample supply port
11: air hole
12: surfactant layer
13, 13a, 13b, 13c: quality deciding section
15, 15': sample receiving section
16, 16a: moisture absorbing material
16b, 16c: moisture absorbing sheet
17: recess
17b: through hole
18: film
19: impermeable cover sheet
20: quality deciding position
21, 22: connectors
23: detecting section
24: measuring section
25: data processing section
26: data displaying section
100, 100a, 100b, 100c: biosensor
200: measuring apparatus
200a: housing
300, 300': analysis disk
301: substrate
302: disk adhering layer
303: disk cover
304: inlet
305: passage
306: reagent
307: air vent hole
313: quality deciding section
316: moisture absorbing material
318: film
320: quality deciding position
411: spindle motor
412: optical pickup
413: feed motor
500: immunosensor
502: supporting substrate
503: liquid collecting section
504: labeled antibody section
505: antibody fixing section
506: nitrocellulose film
507: liquid sucking section
513: quality deciding section
516: moisture absorbing material
518: film
520: quality deciding position
800: liquid injecting instrument
900: sample

BEST MODE FOR CARRYING OUT THE INVENTION

Preferred embodiments of the invention will now be described in detail on the basis of the accompanying drawings. It is noted that a word "connection" herein means "electrical connection" unless otherwise mentioned. Also, elements commonly used in the respective embodiments are referred to by using common reference numerals for simplification.

Embodiment 1

In this embodiment, a biosensor to be used for measuring glucose will be described as an example. As also described later, the present embodiment is not intended to limit the invention to a biosensor for measuring glucose as a test substance.

The biosensor according to this embodiment will be described with reference to FIGS. 1A and 1B. FIG. 1A is an exploded perspective view of the biosensor 100 of this embodiment and FIG. 1B is a cross-sectional view thereof taken on line X-X of FIG. 1A.

As shown in FIGS. 1A and 1B, the biosensor 100 of this embodiment includes a substrate 1 having a quality deciding section 13 and a sample receiving section 15 provided on the substrate 1 to which a sample is supplied. The quality deciding section 13 includes a moisture absorbing material 16 that is changed in color through absorption of moisture. The sample receiving section 15 has a reagent section 7 including an enzyme reacting with a test substance as a substrate.

In this embodiment, the quality deciding section 13 includes a recess 17 formed in the substrate 1, the moisture absorbing material 16 provided in the recess 17 and a film (cover) 18 with no air permeability substantially covering the opening of the recess 17 and closely adhering to the moisture absorbing material 16. Although the film 18 exposes a part of the opening of the recess 17, it covers the most of the opening, and therefore, the air can enter the recess 17 merely through the exposed portion of the opening. Also, since the film 18 has no air permeability, moisture also does not permeate therethrough. In this embodiment, cobalt salt is used as the moisture absorbing material 16. Also, a quality deciding position 20 where the degree of degradation of a reagent is decided in a manner described below is formed on the substrate 1 in the shape of an arrow. In the quality deciding position 20, the moisture absorbing material 16 is covered with the film 18.

In the biosensor 100 of this embodiment, the substrate 1 is made of an electrically insulating material, and the biosensor 100 has terminals 2 and 3 formed on the substrate 1 and terminals 4 and 5 provided in the sample receiving section 15 to be spaced from each other and respectively connected to the terminals 2 and 3. Specifically, the electrode 4 is patterned in a rectangular shape, and the electrode 5 is patterned to be spaced from and to surround the electrode 4. In this embodiment, the electrode 4 and the electrode 5 are respectively covered with conductive carbon pastes 4a and 5a including a resin binder. Furthermore, an insulating film 6 is formed so as to cover a region where a spacer member 8 described below is provided on the substrate 1 and the peripheral portion of the electrode 4, and a portion of the insulating film 6 covering the peripheral portion of the electrode 4 defines the area of an exposed portion of the electrode 4.

The reagent section 7 is provided so as to cover the electrodes 4 and 5 and includes, as a reagent, GOD, that is, an oxidoreductase, and potassium ferricyanide, that is, an electron mediator. In this embodiment, specifically, the reagent section 7 is formed by dropping an aqueous solution of an oxidoreductase of GOD and an electron mediator of potassium ferricyanide onto the electrodes 4 and 5 and drying the aqueous solution. Furthermore, a surfactant layer 12 is formed so as to cover the reagent section 7.

The biosensor of this embodiment further includes the spacer member 8 provided on the substrate 1 and having a slit 10 and a protecting plate 9 provided so as to sandwich the spacer member 8 together with the substrate 1 and having an air hole 11. The slit 10 forms the sample receiving section 15 between the substrate 1 and the protecting plate 9. The air hole 11 of the protecting plate 9 is communicated with the sample receiving section 15, so that a liquid sample can easily reach the reagent section 7 disposed within the sample receiving section 15 through the capillarity by merely bringing the sample liquid into contact with a sample supply port 10a formed on the open end of the slit 10.

In the biosensor 100 of this embodiment, when a sample is allowed to come in contact with the sample supply port 10a, the sample reaches the reagent section 7 provided within the sample receiving section 15 and the surfactant layer 12 is dissolved in the sample in the reagent section 7, so as to cause an enzyme reaction. After a predetermined period of time, when a given potential difference is applied between the terminals 2 and 3 so that the electrode 4 and the electrode 5 can respectively work as a working electrode and a counter electrode, a reductant of the electron mediator resulting from the enzyme reaction is oxidized on the electrode 4. The concentration of glucose contained in the sample can be obtained on the basis of the oxidation current thus caused. At this point, a reaction for reducing an oxidant of the electron mediator to generate the reductant of the electron mediator is proceeded on the electrode 5.

The biosensor 100 of this embodiment was actually used for measuring a glucose concentration by using a solution including a given amount of glucose as a sample. Specifically, when a given period of time elapsed after supplying the sample through the sample supply port 10a to the sample receiving section 15, a voltage of 500 mV on the basis of a voltage on the electrode 5 was applied to the electrode 4. After this voltage application, a value of a current flowing between the electrode 4 and the electrode 5 was measured. Thus, a current response in proportion to the glucose concentration in the sample was observed.

The biosensor 100 of this embodiment is packed in, for example, an arbitrary package in the form of distribution, and immediately after taking it out of the package, the quality deciding section 13 assumes a blue color owing to the moisture absorbing material 16. However, as it is exposed to the air for a longer time, the moisture absorbing material 16 absorbs moisture of the air, and through a reaction with the absorbed moisture, the color of the quality deciding section 13 is gradually changed to a pink color from its portion in contact with the air (i.e., the exposed portion not covered with the film 18). Accordingly, a user can decide to perform measurement when a blue portion of the quality deciding section 13 of the biosensor 100 has a given or larger area, or decide that the biosensor 100 in which a blue portion of the quality deciding section 13 has a smaller area than the given area is not to be used because it is degraded in the reagent section 7 and exchange it with a new biosensor. In this embodiment, in order to further ease this decision, the quality deciding position 20 is provided for showing whether or not a blue portion of the quality deciding section 13 is larger than the given area. Specifically, when a pink portion reaches the quality deciding position 20, it is decided that the reagent has been degraded. Therefore, an ordinary user can always easily use a biosensor having suitable performance without necessity of special knowledge and technique, and accurate measurement can be always performed. The color change of the quality deciding section 13 derives from the property of the cobalt salt used as the moisture absorbing material 16 that it assumes a blue color when dried and assumes a pink color when absorbing moisture. Accordingly, when another material is used as the moisture absorbing material 16, the quality of the biosensor can be decided in accordance with the property in color change of the material between a dry state and a moisture absorbing state. Also, the position and the shape of the quality deciding position 20 are not particularly specified. The quality deciding position 20 shows the degree of degradation of the reagent on the basis of the proportion of a pink portion of the moisture absorbing material 16, and the position for forming the quality deciding position 20 is preferably determined by experimentally deducing a position of the color changed portion of the moisture absorbing material 16 reached when the reagent is too degraded to use by exposing the biosensor 100 of this embodiment to the air. In other words, the position for forming the quality deciding position 20 is determined on the basis of the relationship between a speed of degradation of the reagent through the exposure to the air and a speed of color change of the quality deciding section 13 gradually caused from its portion in contact with the air.

The color change of the quality deciding section 13 may be visually checked by a measurer, which does not limit the invention. For example, a device for detecting the color change of the quality deciding section 13 may be used. An example of such a device will be described in detail in Embodiment 2 below. The position of the quality deciding section 13 is not limited to that described in this embodiment.

Also, the moisture absorbing material 16 of this embodiment may be any substance that is changed in color through absorption of moisture. For example, cobalt salt such as cobalt chloride or cobalt bromide may be used. Also, the moisture absorbing material 16 is further preferably a substance in which the reaction for changing its color through the absorption of moisture is irreversible. When the moisture absorbing material is such a substance, the contact state between the biosensor 100 and the moisture of the air can be more definitely determined. For example, in using blue silica gel, when it is once changed in color from blue to pink through the absorption of moisture, it is necessary to heat it for discharging the absorbed moisture, and hence, the reverse reaction (i.e., the reaction for discharging the moisture) is proceeded slowly at room temperature. Therefore, it is suitably used for making determination by the color change as in this invention.

Also, the voltage applied to the electrode 4 is 500 mV on the basis of the voltage of the electrode 5 in this embodiment, which does not limit the invention, but the voltage may be any voltage at which the electron mediator can react on the electrode 4.

As described above, the biosensor for measuring glucose by using a β-D-glucose aqueous solution as a sample is described as an example in this embodiment, which does not limit the invention. For example, a biological sample such as whole blood, blood plasma, blood serum, interstitial fluid, saliva or urine may be used.

Furthermore, the test substance of the biosensor 100 of this embodiment is not limited to glucose. For example, the test substance of the biosensor may be a substance included in a biological sample such as whole blood, blood plasma, blood serum, interstitial fluid, saliva or urine. It is noted that whole blood herein means blood that has not been subjected to special processing, such as capillary blood, venous blood or arterial blood obtained by tapping, for example, a finger tip or a skin of an arm.

In the case where the test substance is a substance other than glucose and the biosensor utilizes an enzyme reaction, it is necessary to select an enzyme reacting with the test substance as a substrate. Although GOD, that is, an oxidoreductase, is used as the enzyme included in the reagent section 7 in this embodiment, an oxidoreductase other than GOD (such as fructose dehydrogenase, glucose dehydrogenase, alcohol oxidase, lactate oxidase, cholesterol oxidase, xanthine oxidase or amino acid oxidase) may be used.

Examples of the electron mediator are potassium ferricyanide, p-benzoquinone, phenazine methosulfate, methylene blue, a ferrocene derivative and the like. Also in the case where oxygen is used as the electron mediator, a current response can be obtained. Instead of using one of these substances as the electron mediator, a combination of two or more of them may be used.

Next, a method for fabricating the biosensor 100 of this embodiment will be simply described.

First, a silver paste or the like is printed by screen printing on an electrically insulating substrate 1 of poly(ethylene terephthalate) or the like in which a recess 17 is previously formed, thereby forming a terminal 2 and a terminal 3. Subsequently, a conductive carbon paste including a resin binder is printed on the substrate 1, thereby forming an electrode 4 connected to the terminal 2. Thereafter, an insulating paste is printed on the substrate 1, thereby forming an insulating film 6 that covers the peripheral portion of the electrode 4 so as to define the area of an exposed portion of the electrode 4.

Next, a conductive carbon paste including a resin binder is printed on the substrate 1, thereby forming an electrode 5 connected to the terminal 3.

Then, an aqueous solution including an oxidoreductase of GOD and an electron mediator of potassium ferricyanide is dropped on the electrode 4 and the electrode 5, and the solution is dried so as to form a reagent section 7. Thereafter, a surfactant layer 12 including lecithin, that is, a surfactant, is formed on the reagent section 7.

Next, a spacer member 8 is adhered on the insulating film 6, and a protecting plate 9 having an air hole 11 is adhered on the spacer member 8.

Ultimately, a moisture absorbing material 16 of cobalt salt is put in the recess 17 of the substrate 1 and a film 18 is adhered onto the substrate 1, thereby forming a quality deciding section 13. Thereafter, the resultant biosensor 100 is immediately packed in a package containing a desiccant for storage.

The GOD is used as the enzyme and the potassium ferricyanide is used as the electron mediator in the reagent section 7 of this embodiment, which does not limit the invention. Other specific examples of the enzyme and the electron mediator are described above.

Furthermore, the reagent section 7 is formed by applying and drying the solution including the oxidoreductase in this embodiment, which does not limit the invention. For example, a solution including an oxidoreductase may be applied by an ink jet method. In this case, even when a small amount of solution is applied, the position for forming the reagent section 7 can be accurately controlled. Alternatively, with a solution including an oxidoreductase held on glass filter paper, the glass filter paper may be dried and provided in the sample receiving section 15, or an oxidoreductase may be held in the sample receiving section 15 by a freeze-dry method. Further alternatively, the electrode may be formed by mixing a conductive material and a reagent.

The reagent section 7 is preferably positioned on the electrode 4 or the electrode 5, which does not limit the invention, but it may be positioned in any place in the sample supplying section 15 other than on the electrode 4 or the electrode 5 as far as it can come into contact with a sample.

In this embodiment, the substrate 1 and the spacer member 8 may be made of any material that has an electric insulating property and has sufficient rigidity for storage of the biosensor 100 and measurement with the biosensor. Examples of the material for the substrate 1 are a thermoplastic resin such as poly(ethylene terephthalate), polyethylene, polystyrene, poly(vinyl chloride), polyamide or a saturated polyester resin, and a thermosetting resin such as a urea resin, a melamine resin, a phenol resin, an epoxy resin or an unsaturated polyester resin. In particular, poly(ethylene terephthalate) is preferably used for the substrate 1 from the viewpoint of adhesion to the electrode.

Also, the spacer member 8 and the protecting plate 9 are preferably made of a light blocking material. Thus, the enzyme and the electron mediator included in the reagent section 7 can be protected from light such as UV that may harmfully affect them.

The terminals 2 and 3 and the electrodes 4 and 5 are formed by the screen printing in this embodiment, which does not limit the invention. For example, a method in which a noble metal such as palladium is sputtered onto the substrate and an electrode pattern is formed by laser trimming or a method in which an electrode pattern is formed by photolithography may be employed.

The electrodes 4 and 5 may be made of any conductive material that is not oxidized through oxidation of the electron mediator. Examples of the material are carbon, palladium, gold and platinum. Alternatively, the electrode may be formed by covering an electric insulating material with such a conductive material.

Furthermore, the position of the air hole 11 is not limited to that shown in the drawing, but the air hole 11 may be provided in any place that is communicated with the sample receiving section 15 and where the capillarity is caused for introducing a sample from the sample supply port 10a to the sample receiving section 15. Specifically, it is positioned on one end of the slit 10 opposite to the sample supply port 10a.

Embodiment 2

A biosensor according to this embodiment will be described with reference to FIGS. 2A and 2B. FIG. 2A is an exploded perspective view of the biosensor 100a of this embodiment and FIG. 2B is a cross-sectional view thereof taken on line Y-Y of FIG. 2A.

As shown in FIGS. 2A and 2B, the biosensor 100a of this embodiment has substantially the same structure as the biosensor 100 of Embodiment 1 described above and is different in a quality deciding section 13a alone from the biosensor 100.

The quality deciding section 13a is made of a sheet material including a moisture absorbing material 16a and is adhered onto a substrate 1. More specifically, the moisture absorbing material 16a in the shape of a sheet is adhered onto the substrate 1, and a film 18 is adhered so as to cover most of the moisture absorbing material 16a. The film 18 is made of a material having no air permeability and is closely adhered to the moisture absorbing material 16a. Also, one end of the moisture absorbing material 16a is not covered with the film 18 but is exposed. It is noted that cobalt salt is used as the moisture absorbing material 16a. In the structure of this embodiment, since there is no need to form a recess or the like in the substrate 1, the fabrication of the biosensor is eased.

Needless to say, also when the biosensor 100a of this embodiment is used, since a quality deciding position 20 is provided, an ordinary user can always easily use a biosensor having performance suitable for use without necessity of special knowledge and technique, and hence, accurate measurement can be always performed.

Embodiment 3

A biosensor according to this embodiment will be described with reference to FIGS. 3A and 3B. FIG. 3A is an exploded perspective view of the biosensor 100b of this embodiment and FIG. 3B is a cross-sectional view thereof taken on line Z-Z of FIG. 3A.

As shown in FIGS. 3A and 3B, the biosensor 100b of this embodiment has substantially the same structure as the biosensor 100 of Embodiment 1. However, the biosensor 100b is different from the biosensor 100 in the following points: A substrate 1 has a through hole 17b, a moisture absorbing sheet 16b made of a moisture absorbing material is adhered to a lower face of the substrate 1, a transparent impermeable cover sheet 19 is adhered to the lower face of the moisture absorbing sheet 16b, a quality deciding section 13b is provided on the side of the lower face of the substrate, and a quality deciding position 20 is also provided on the side of the lower face of the substrate 1. It is noted that a sheet material including cobalt salt is used as the moisture absorbing sheet 16b.

In this embodiment, the proceeding degree of the color change of the moisture absorbing sheet 16b can be determined through the transparent impermeable cover sheet 19. Specifically, since the moisture absorbing sheet 16b is exposed in the through hole 17b, the air enters through this exposed portion and the moisture of the air is absorbed by the moisture absorbing material, and hence, the color of the moisture absorbing sheet 16b is changed from blue to pink from its exposed portion in the through hole 17b. The spread of this color change can be observed through the transparent impermeable cover sheet 19.

Needless to say, also when the biosensor 100b of this embodiment is used, an ordinary user can always easily use a biosensor with performance suitable for use without necessity of special knowledge and technique, and accurate measurement can be always performed.

In particular, the biosensor 100b of this embodiment can be easily fabricated. This will be described with reference to FIGS. 4A and 4B. FIGS. 4A and 4B are cross-sectional views for showing procedures in a fabrication method for the biosensor 100b of this embodiment.

First, in the procedure shown in FIG. 4A, a silver paste or the like is printed on an electrically insulating substrate 1 of poly(ethylene terephthalate) or the like in which a through hole 17b is previously formed, thereby forming terminals 2 and 3. Subsequently, a conductive carbon paste including a resin binder is printed on the substrate 1, thereby forming an electrode 4 connected to the terminal 2. Thereafter, an insulating paste is printed on the substrate 1, thereby forming an insulating film 6 covering the peripheral portion of the electrode 4 so as to define the area of an exposed portion of the electrode 4. Then, a conductive carbon paste including a resin binder is printed on the substrate 1, thereby forming an electrode 5 connected to the terminal 3.

Subsequently, an aqueous solution including GOD, that is, an oxidoreductase, and potassium ferricyanide, that is, an electron mediator, is dropped on the electrode 4 and the electrode 5, and the solution is dried so as to form a reagent section 7. Thereafter, a surfactant layer 12 including lecithin, that is, a surfactant, is formed on the reagent section 7. Then, a spacer member 8 is adhered onto the insulating film 6, and a protecting plate 9 having an air hole 11 is adhered onto the spacer member 8.

Next, in the procedure shown in FIG. 4B, a moisture absorbing sheet 16b is adhered to the lower face of the substrate 1, and a transparent impermeable cover sheet 19 (which is a plastic sheet in this embodiment) is adhered to the entire lower face of the moisture absorbing sheet 16b. Thus, a quality deciding section 13b is formed. A mark of a quality deciding position 20 is previously printed on the impermeable cover sheet 19.

In the case where a plurality of biosensors 100b are fabricated at one time on one substrate in each of the aforementioned procedures, the substrate is ultimately divided into the respective biosensors 100b.

Thereafter, each biosensor 100b is immediately packed in a package containing a desiccant for storage.

As described above, in the fabrication of the biosensor 100b of this embodiment, after forming a plurality of biosensors 100b at one time on one substrate, the substrate can be ultimately divided into the respective biosensors 100b. Therefore, a large number of biosensors 100b can be easily fabricated.

Also, in the fabrication of the biosensor 100b of this embodiment, the process for forming the quality deciding section 13b can be extremely simplified (or substantially eliminated). Accordingly, time when the moisture absorbing sheet 16b is exposed to the air can be largely reduced, and hence, the moisture absorption of the moisture absorbing sheet 16b during the fabrication can be extremely suppressed. Therefore, it can be more accurately decide whether or not the reagent section 7 of the biosensor 100b has performance suitable for use.

Embodiment 4

Figure 5:
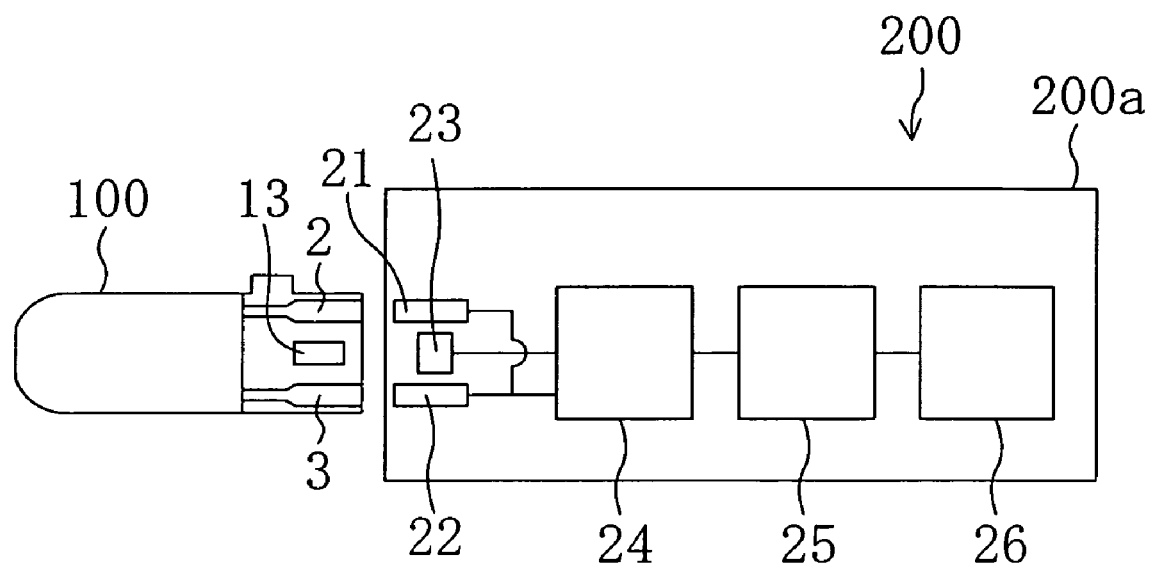
FIG. 5 is a schematic perspective view for showing the structure of a biosensor measuring apparatus according to Embodiment 4 in which a biosensor to be fitted thereon is schematically shown.

In this embodiment, a biosensor measuring apparatus to be connected to the biosensor 100 of Embodiment 1 for use will be described with reference to FIGS. 5 and 6. FIG. 5 is a schematic perspective view for showing the structure of the biosensor measuring apparatus of this embodiment and schematically shows a biosensor to be fitted thereon. FIGS. 6A and 6B are cross-sectional views for schematically showing the operation of the biosensor measuring apparatus of this embodiment performed in measurement with the biosensor.

As shown in FIG. 5, the biosensor measuring apparatus 200 of this embodiment includes a pair of connectors 21 and 22, a detecting section 23, a measuring section 24 connected to the pair of connectors 21 and 22 and the detecting section 23, a data processing section 25 connected to the measuring section 24, and a data displaying section 26 connected to the data processing section 25. In this embodiment, the pair of connectors 21 and 22, the detecting section 23, the measuring section 24, the data processing section 25 and the data displaying section 26 are housed in a housing 200a. The housing 200a has a slot (not shown) through which the biosensor 100 can be inserted.

The pair of connectors 21 and 22 are respectively connected to the terminal 2 and the terminal 3 of the biosensor 100 when the biosensor 100 is fitted on the biosensor measuring apparatus 200.

When the biosensor 100 is fitted through the slot of the biosensor measuring apparatus 200, the detecting section 23 detects the color change of the portion of the quality deciding section 13 corresponding to the quality deciding position 20 and outputs the thus obtained optical characteristic to the measuring section 24. The detecting section 23 of this embodiment has a light source and a photo detecting device, and is provided, as shown in FIG. 6A, so that the light source can emit light to the portion of the quality deciding section 13 of the biosensor 100 corresponding to the quality deciding position 20 and that light reflected by the portion corresponding to the quality deciding position 20 can enter the photo detecting device. As the light source, a light emitting diode, a semiconductor laser or the like is used, and as the photo detecting device, a photo diode, a photo transistor or the like is used. The photo detecting device detects the incident light entering from the portion of the quality deciding section 13 corresponding to the quality deciding position 20.

The measuring section 24 measures, on the basis of the output from the detecting section 23, optical characteristic data such as a wavelength spectral pattern of the incident light or the intensity of light of a specific wavelength and determines, on the basis of the obtained optical characteristic data, whether or not the degradation degree of the reagent section 7 of the biosensor 100 is suitable for measurement, and in the case where the performance of the reagent section 7 is suitable for the measurement, a value of a current flowing between the electrode 4 and the electrode 5 is measured through the pair of connectors 21 and 22. For example, in the case where the biosensor 100 of the embodiment is connected for use, when the detecting section 23 detects that the color of the portion of the quality deciding section 13 corresponding to the quality deciding position 20 is blue, the measurement is performed after a measurement standby state, so as to output measured data to the data processing section 25. If the detecting section 23 detects that the color of the portion of the quality deciding section 13 corresponding to the quality deciding position 20 is pink, data that the biosensor is unsuitable for the measurement is output to the data processing section 25.

When the measured data is input, the data processing section 25 digitizes the measured data and outputs the digitized data to the data displaying section 26. When the data that the biosensor is unsuitable for the measurement is input, the data processing section 25 outputs an instruction for making the data displaying section 26 display that the biosensor is unsuitable for the measurement.

The data displaying section 26 produces a display in accordance with the data or the instruction output from the data processing section 25.

In particular, in this embodiment, when the biosensor 100 is fitted in the slot of the biosensor measuring apparatus 200, the quality deciding section 13 of the biosensor 100 is disposed within the biosensor measuring apparatus 200. Therefore, the color change of the quality deciding section 13 can be detected in the detecting section 23 of the biosensor measuring apparatus 200, so as to determine whether or not the biosensor is suitable for use. When the biosensor 100 and the biosensor measuring apparatus 200 are thus used, a measurer can automatically perform accurate measurement without necessity of special knowledge.

At this point, examples of the positional relationship between the detecting section 23 provided in the biosensor measuring apparatus 200 and the biosensor 100 will be shown in FIGS. 6A and 6B.

As shown in FIG. 6A, in the detecting section 23 of the biosensor measuring apparatus 200 of this embodiment, the light source of the detecting section is disposed above the quality deciding section 13 of the biosensor 100, and the photo detecting device is disposed in a position for receiving light emitted from the light source and reflected at approximately 45 degrees. Thus, the color change of the quality deciding section 13 (namely, the moisture absorbing material 16) is detected on the basis of the reflected light.

Alternatively, as shown in FIG. 6B, the light source and the photo detecting device of the detecting section 23 may be disposed so as to sandwich a biosensor 100c for measuring light passing through a quality deciding section 13c. In this case, both a substrate 1c and an impermeable cover sheet 19 are transparent against light emitted from the light source.

The biosensor 100c of FIG. 6B has substantially the same structure as the biosensor 100b of Embodiment 3 and is different from the biosensor 100b of Embodiment 3 in the substrate 1c of the biosensor 100c being transparent. Since the substrate 1c is transparent, the light emitted from the light source passes through the substrate 1c, passes through a moisture absorbing sheet 16c, passes through the impermeable cover sheet 19 and enters the photo detecting device.

The quality deciding section 13 of the biosensor 100 is disposed between the electrode 4 and the electrode 5 in this embodiment, which does not limit the invention. The position of the quality deciding section 13 is not particularly specified as far as it is disposed within the biosensor measuring apparatus 200 when the biosensor 100 is fitted in the slot of the biosensor measuring apparatus 200 and the detecting section 23 can detect the color change of a portion of the moisture absorbing material 16 of the quality deciding section 13 corresponding to the quality deciding position 20.

Also, although the biosensor 100 is fitted on the biosensor measuring apparatus 200 in this embodiment, it goes without saying that the biosensor 100a or 100b of Embodiment 2 or 3 may be fitted thereon for use. However, when the biosensor 100b of Embodiment 3 is used, a biosensor measuring apparatus in which a light source and a photo detecting device are disposed on the side of the lower face of the biosensor 100b is used.

Embodiment 5

Figure 7:
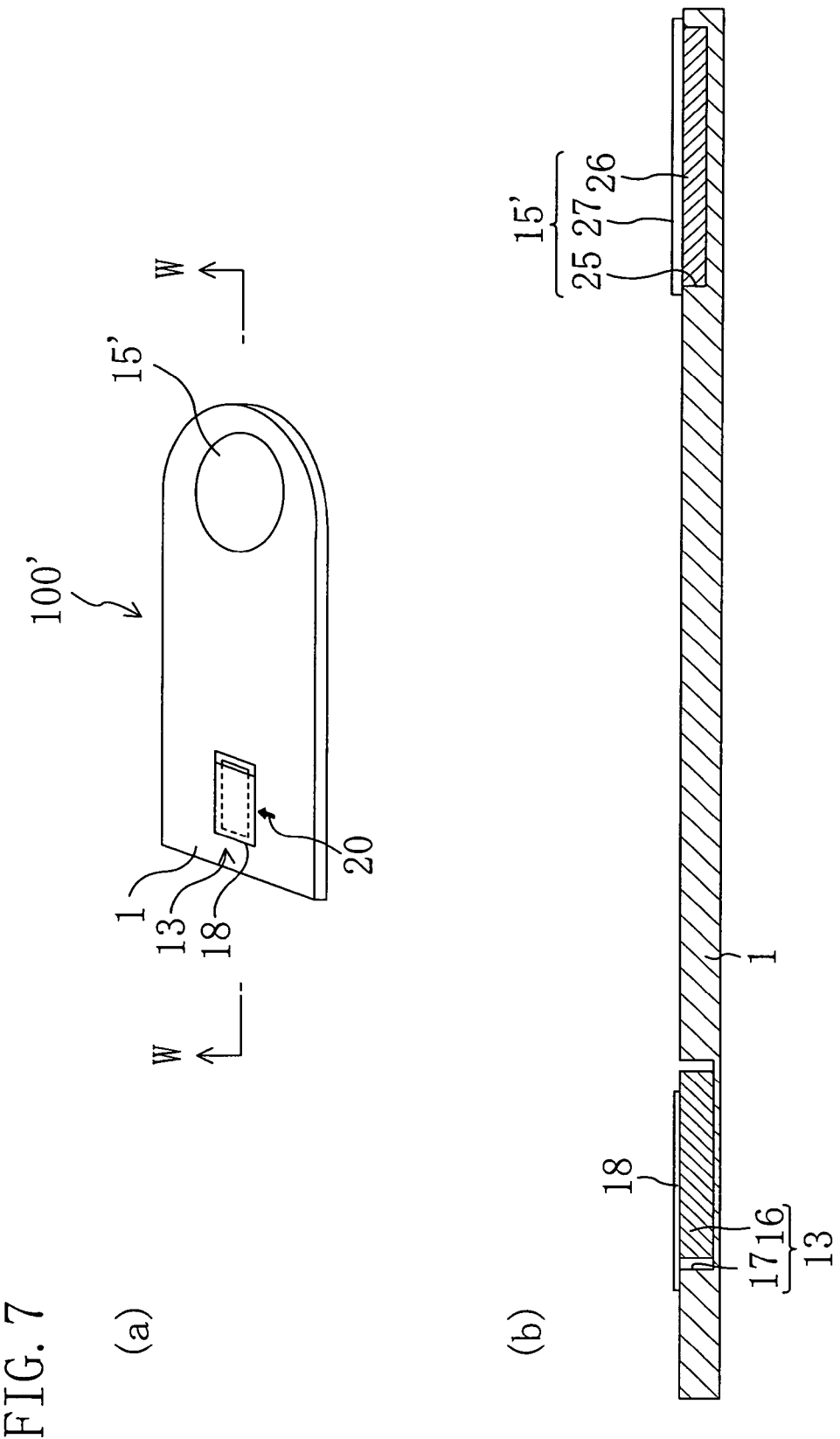
FIG. 7A is a perspective view of a biosensor according to Embodiment 5 and FIG. 7B is a cross-sectional view thereof taken on line W-W of FIG. 7A.

Each of the biosensors 100, 100a, 100b and 100c of Embodiments 1 through 4 has a structure in which a test substance is electrochemically detected (namely, the biosensors are electrochemical biosensors), which does not limit the invention. Now, an example of a biosensor having another structure will be described with reference to FIGS. 7A and 7B. FIG. 7A is a perspective view of a biosensor 100' for optically detecting a test substance and FIG. 7B is a cross-sectional view thereof taken on line W-W of FIG. 7A.

As shown in FIGS. 7A and 7B, the biosensor 100' includes a substrate 1 having a quality deciding section 13 and a sample receiving section 15' provided on the substrate 1 to which a sample is supplied. The quality deciding section 13 includes a moisture absorbing material that is changed in color through absorption of moisture.

In the biosensor 100', the quality deciding section 13 includes a recess 17 formed in the substrate 1, the moisture absorbing material 16 provided in the recess 17 and a film (cover) 18 with no air permeability provided so as to substantially cover the opening of the recess 17 and to be closely adhered to the moisture absorbing material 16, which structure is completely the same as that of the biosensor 100 of Embodiment 1 described above. It is noted that cobalt salt is used as the moisture absorbing material 16.

The sample receiving section 15' includes a recess 25 formed in the substrate 1, a reagent section 26 provided in the recess 25 and including an enzyme reacting with a test substance as a substrate and a permeable film 27 provided so as to cover the opening of the recess 25 and capable of permeating moisture. In particular, in the biosensor 100' of this embodiment, the test substance is detected by measuring the color change of the sample receiving section 15'. The reagent section 26 employs, for example, a structure in which the included enzyme assumes a color or fluoresces through an enzyme reaction, a structure further including a pH indicator that assumes a color through change of pH caused by an enzyme reaction, a structure in which color change is caused by reduction of the substrate through an enzyme reaction or the like.

Also in the biosensor 100' for optically detecting a test substance, since the quality deciding section 13 is provided in the same manner as in each biosensor of Embodiments 1 through 3, a user can determine whether or not the reagent section 26 of the biosensor 100' is in a suitable state for the measurement.

Embodiment 6

Furthermore, in the biosensor of each of Embodiments 1 through 3 described above, the quality deciding section is provided on a biosensor having the structure in which a liquid sample allowed to come in contact with the sample supply port is sucked through the capillary so as to come in contact with the reagent for enabling the measurement, but the invention is not limited to this structure. Now, examples of an analysis disk in which, with a cavity for containing a liquid provided on a rotatable disk, the liquid is analyzed by rotating the disk with the liquid contained therein will be described with reference to FIG. 8.

As shown in FIGS. 8A and 8B, a biosensor of this embodiment is in the shape of a disk, and a quality deciding section 313 is provided on an analysis disk 300 or 300'. The quality deciding section 313 includes a sheet-shaped moisture absorbing material 316 similar to that described in Embodiment 2, a film 318 and a quality deciding position 320. The quality deciding section 313 is adhered onto the disk 300. It is noted that the analysis disk 300 of FIG. 8A and the analysis disk 300' of FIG. 8B are different from each other in the position of the quality deciding section 313. In the analysis disk 300 of FIG. 8A, a distance from the center of the disk to the quality deciding section 320 is equal to a distance from the center of the disk to a reagent 306 described below. On the other hand, in the analysis disk 300' of FIG. 8B, the quality deciding section 313 may be provided in any position except for a position above the reagent 306.

As shown in FIG. 8C, the disk 300 or 300' of this embodiment includes a disk substrate 301, a disk adhering layer 302 and a disk cover 303. The disk cover 303 is made of a transparent material. The disk is provided with an inlet 304 and a passage 305 corresponding to a cavity, and the passage 305 is coated with the reagent 306 whose optical characteristic (such as transmittance or color) is changed through a reaction with a sample. The analysis is performed with the disk 300 or 300' fitted on an analysis apparatus after injecting a sample 900 into the disk 300 or 300' with a liquid injection instrument 800 such as a pipette or a syringe through the inlet 304. The passage 305 has an air vent hole 307 for easily injecting the sample 900.

Figure 9:
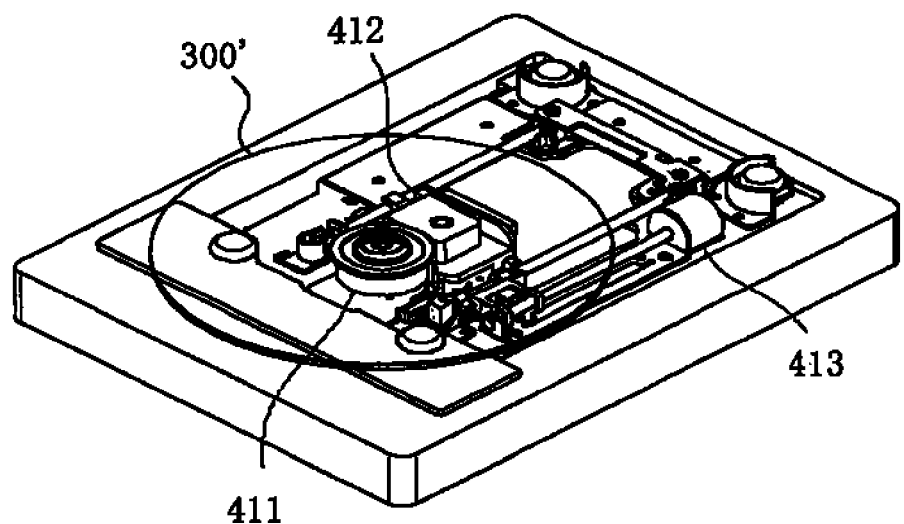
FIG. 9 is a schematic perspective view for showing the structure of a measuring apparatus for the biosensor of FIG. 8B.

FIG. 9 is a perspective view for showing the internal structure of the analysis apparatus used for analyzing the analysis disk 300' of FIG. 8B. In FIG. 9, the analysis disk 300' is transparent for clearly showing the internal structure of the apparatus. The structure of the apparatus is similar to that of the so-called optical disk drive, and the apparatus includes a spindle motor 411 for rotating the disk 300', an optical pickup 412 for irradiating, with light beams, the sample 900 spread in the disk 300' or the reagent 306 having reacted with the sample 900, a feed motor 413 for moving the optical pickup 412 along the radial direction of the disk 300' and the like. Also, the optical pickup 412 irradiates a portion of the moisture absorbing material 316 corresponding to the quality deciding position 320 with light.

The disk 300' fitted on the apparatus is driven by the spindle motor 411 to rotate, but before the rotation, the optical pickup 412 is moved by the feed motor 413, the disk 300' is rotated so that the quality deciding position 320 can be placed above the optical pickup 412, and thus, the absorbance of the portion of the moisture absorbing material 316 corresponding to the quality deciding position 320 is first measured for determining the quality. In the case where the reagent 306 is decided to be degraded at this point, an error occurs so as not to perform the following measurement. This operation is similar to the operation of the analysis apparatus described in Embodiment 4.

Next, the disk 300' is driven by the spindle motor 411 to rotate, and hence, the sample 900 having been injected through the inlet 304 provided on the inner diameter side of the disk 300' is spread within the passage 305 of the disk 300' through centrifugal force so as to proceed toward the air vent hole 307 provided on the outer diameter side of the disk 300'. At this point, the sample 900 reacts with the reagent 306 coated on the passage 305, thereby causing an enzyme reaction or an immune reaction. After the reaction is completed, the optical pickup 412 is used for irradiating, with the light beams, the sample 900 or the reagent 306 present within the passage 305 while rotating the disk 300', and the reaction state of the reagent 306 is detected by detecting reflected light or transmitted light for quantitative or qualitative analysis.

Since the analysis disk 300' of this embodiment includes the quality deciding section 313, after fitting the analysis disk 300' on the analysis apparatus of FIG. 9, the quality is first determined by using the optical pickup 412 before rotating the disk. In the case where the reagent 306 is decided to be degraded at this point, an error occurs so as not to perform the following measurement.

In this manner, the degree of degradation of the reagent can be decided also with respect to the analysis disk for performing the analysis of a liquid through the rotation, and hence, more accurate measurement can be performed.

Also, in the analysis apparatus used for analyzing the analysis disk 300 of FIG. 8A, since the quality deciding position 320 is provided in the same position along the radial direction of the disk as the position where the reagent 306 is provided, there is no need to move the optical pickup 412 along the radial direction. Accordingly, this analysis apparatus does not need the feed motor 413 and hence can be fabricated inexpensively and in a compact shape. Also, the time necessary for the measurement can be reduced.

Furthermore, also in this embodiment, the analysis of a sample is not limited to that performed through the optical measurement but may be performed through electrical measurement or the like.

Embodiment 7

In each of the biosensors of Embodiments 1 through 3 described above, the quality deciding section is provided to a biosensor utilizing an enzyme reaction as a reagent, which does not limit the invention. Now, a biosensor utilizing an immune reaction will be described with reference to FIG. 10.

Figure 10:
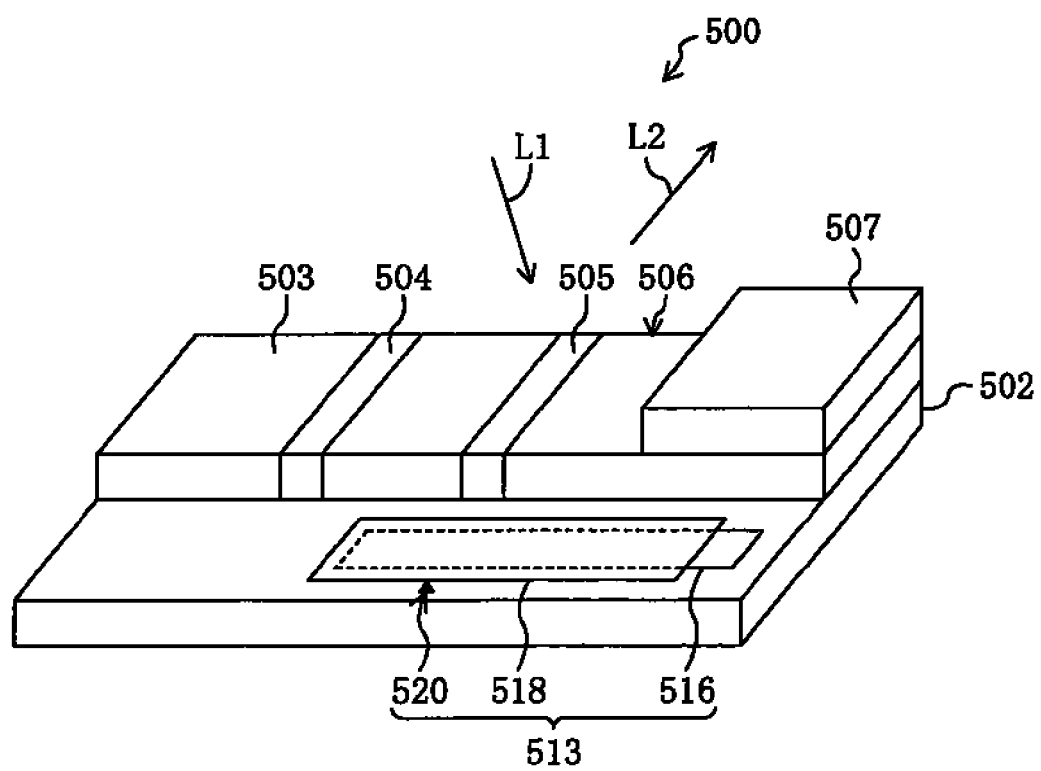
FIG. 10 is a perspective view of a biosensor according to Embodiment 7.

As shown in FIG. 10, a biosensor of this embodiment is an immunosensor 500, in which a quality deciding section 513 is present on a plastic supporting substrate 502. The quality deciding section 513 includes a sheet-shaped moisture absorbing material 516 similar to that described in Embodiment 2, a film 518 and a quality deciding position 520. Also, the quality deciding section 513 is adhered onto the plastic supporting substrate 502.

FIG. 10 schematically shows the structure of the immunosensor 500. In this immunosensor 500, a nitrocellulose film 506 is provided on the plastic supporting substrate 502. The nitrocellulose film 506 includes a liquid collecting section 503, a labeled antibody section 504 and an antibody fixing section 505. The liquid collecting section 503 is formed on one end of the nitrocellulose film 506 in the shape of a strap. The labeled antibody section 504 is formed by coating the nitrocellulose film 506 with a pigment labeled antibody. The pigment labeled antibody is coated to be flowable from the labeled antibody section 504. The pigment labeled antibody selectively absorbs light of a given wavelength (of, for example, 550 nm). Also, in the antibody fixing section 505, another antibody reactive with an antigen with which the pigment labeled antibody reacts is fixed in a state that it cannot flow to the nitrocellulose film 506. Furthermore, a glass fiber filter paper for sucking a sample liquid is provided as a liquid sucking section 507 on the nitrocellulose film 506 on the end opposite to the liquid collecting section 503.

Measurement of absorbance using this immunosensor 500 is performed, for example, as follows: When a sample such as urine is supplied to the liquid collecting section 503, the sample moves toward the liquid sucking section 507 through the principle of chromatography. During this movement of the sample, the pigment labeled antibody is coupled to an antigen included in the sample first in the labeled antibody section 504. Since the pigment labeled antibody can flow out of the labeled antibody section 504, the antigen coupled to the pigment labeled antibody moves together with the sample to the antibody fixing section 505 and is coupled to the fixed antibody to stay therein. When the antibody fixing section 505 is irradiated with light L1 of the given wavelength and resultant reflected light L2 is measured, the absorbance can be measured. Since the amount of pigment labeled antibody stayed in the antibody fixing section 505 depends upon the amount (concentration) of the antigen in the sample, the concentration of the antigen included in the sample can be determined on the basis of the thus measured absorbance.

The immunosensor 500 of this embodiment includes the quality deciding section 513. Accordingly, before performing the measurement of the sample by using an analysis apparatus, a portion of the moisture absorbing material 516 corresponding to the quality deciding position 520 is irradiated with light, so as to measure the absorbance of the moisture absorbing material 516 in the quality deciding position 520, and thus, the quality of reagents (i.e., the pigment labeled antibody and another fixed antibody) can be determined based on the absorbance. In the case where the reagents are decided to be degraded at this point, an error occurs so as not to perform the measurement. This operation is similar to the operation of the analysis apparatus described in Embodiment 4. Since the quality deciding position 520 is provided to be adjacent to the antibody fixing section 505 in this embodiment, the optical system used for measuring a sample can be directly used for the quality decision.

In this manner, the degree of degradation of reagents can be decided also in a biosensor utilizing an immune reaction in this embodiment, and therefore, more accurate measurement can be performed.

Although an antigen is a test substance in this embodiment, an antibody may be a test substance. In this case, the pigment labeled antibody is replaced with a pigment labeled antigen, and the antibody fixing section is replaced with an antigen fixing section in which an antigen specifically reactive with an antibody of the test substance is fixed.

Antibodies and antigens to be used in this embodiment are not particularly specified. They may be any substance that can be generally measured by using an antigen-antibody reaction. Examples of such a substance are proteins, nucleic acid, lipids, bacterium, virus and hapten. Among these substances, proteins can be suitably used because they are principal targets of measurement in a laboratory test using an antigen-antibody reaction. Examples of proteins preferably used in this embodiment are hormones such as LH (luteinizing hormone), FSH (follicle stimulating hormone) or hCG (human chorionic gonadotrophic), various immunoglobulins and their subclasses, complement components, markers of various infections, C-reactive proteins, albumin, rheumatoid factors and blood group antigens. Furthermore, any antibody specifically reacting with an antigen can be used, and an example of the antibody is a mouse-derived monoclonal antibody, which does not limit the invention.

As the pigment used for labeling the antibody, for example, a cyanine pigment having a functional group with high reactivity can be used.

Also, although an immunosensor having a structure in which an antibody is fixed in the nitrocellulose film 506 and the principle of the chromatography is utilized is described in this embodiment, the shape of the sensor is not limited to this. For example, the sensor may be an immunosensor having a structure for measuring immunophelometry or a biosensor in which a reagent is held in a dry state, to which a quality deciding section is further provided.

INDUSTRIAL APPLICABILITY

As described so far, the biosensor and the biosensor measuring apparatus of this invention are useful for measurement or the like performed in a medical diagnosis in which it is necessary to more accurately measure a test substance included in a sample.

The invention claimed is:

1. A measurement method for measuring a test substance in a sample using a biosensor in a sealed package, said biosensor comprising a substrate having a sample receiving section, a reagent section including a reagent; and a colorimetric moisture absorbing indicating material, the method of using the biosensor comprising the steps of:
    removing said biosensor from said package;
    determining a degree of degradation of said reagent on the basis of a degree of color change of said colorimetric moisture absorbing indicating material; and
    measuring said test substance when the degree of degradation of said reagent is determined to be acceptable in the determining step and not measuring said test substance when the degree of degradation of said reagent is determined to be unacceptable.

2. The measurement method of claim 1, wherein the biosensor further comprises a cover for covering said colorimetric moisture absorbing indicating material,
    wherein a part of said colorimetric moisture absorbing indicating material is exposed.

3. The measurement method of claim 2, wherein the degree of degradation of said reagent is based on a degree of color change of a portion of said colorimetric moisture absorbing indicating material that is present at a given distance from the exposed part and is covered with said cover.

4. The measurement method of claim 1, wherein said reagent includes an enzyme.

5. The measurement method of claim 4, wherein said reagent section further includes an electron mediator.

6. The measurement method of claim 5, wherein said biosensor further comprises:
   a pair of terminals provided on said substrate; and
   a pair of electrodes provided in said sample receiving section to be spaced from each other and respectively connected to said pair of terminals.

7. The measurement method of claim 1, wherein said reagent includes at least one of an antibody and an antigen.

8. The measurement method of claim 1, wherein said colorimetric moisture absorbing indicating material is in the shape of a sheet.

9. The measurement method of claim 1, wherein said biosensor further comprises a covering member made of a light blocking material and formed over said substrate for covering said sample receiving section.

10. The measurement method of claim 8,
   wherein said colorimetric moisture absorbing indicating material in the shape of a sheet is provided on a face of said substrate opposite to a face thereof on which said sample receiving section is provided, and
   a sheet for covering said colorimetric moisture absorbing indicating material is provided on said moisture absorbing material.

* * * * *